United States Patent
Mathews et al.

[11] Patent Number: 6,151,952
[45] Date of Patent: Nov. 28, 2000

[54] SYSTEM FOR MASS EMISSION SAMPLING OF COMBUSTION PRODUCTS

[75] Inventors: Loren T. Mathews, Yorba Linda; David B. White, Lake Forest; David R. Whineray, Placentia, all of Calif.

[73] Assignee: California Analytical Instruments, Inc., Orange, Calif.

[21] Appl. No.: 09/178,800

[22] Filed: Oct. 26, 1998

[51] Int. Cl.[7] .................................................. G01N 1/00
[52] U.S. Cl. ................................... 73/23.31; 73/863.33
[58] Field of Search .............................. 73/1.06, 863.03, 73/863.01, 863.12, 863.33, 804.81, 23.21–23.33

[56] References Cited

U.S. PATENT DOCUMENTS

| | | |
|---|---|---|
| 3,917,454 | 11/1975 | Clark . |
| 4,191,541 | 3/1980 | Jenkins . |
| 4,386,534 | 6/1983 | Englund et al. . |
| 4,747,297 | 5/1988 | Okayama et al. . |
| 4,779,466 | 10/1988 | Ramsner et al. . |
| 5,450,749 | 9/1995 | Strom et al. . |
| 5,469,731 | 11/1995 | Decker et al. ................ 73/863.03 |
| 5,731,510 | 3/1998 | Jones et al. . |
| 5,739,413 | 4/1998 | Kohn et al. . |
| 5,756,360 | 5/1998 | Harvey et al. . |
| 5,835,974 | 11/1998 | Nagy . |

*Primary Examiner*—Robert Raevis
*Attorney, Agent, or Firm*—John E. Vanderburgh

[57] ABSTRACT

An emission testing system particularly suited for vehicle emission testing. The system includes at least one research grade non-dispersive infrared (NDIR) unit, a chemiluminescence detector (CLD) unit and a flame ionization detection (FID) unit. All of the analytical units are incorporated in the system for operation with a sample which has been subjected to a single conditioning step. In this manner each analytical unit tests a uniformly conditioned sample. The system is capable of sampling both raw emissions for raw emission idle tests (BAR 90) and dilute volume samples for dilute volume sample mass emission tests under IM-240 regulations.

13 Claims, 5 Drawing Sheets

SYSTEM FOR MASS EMISSION SAMPLING OF COMBUSTION PRODUCTS

FIELD OF THE INVENTION

This invention relates to apparatus for testing gases and more particularly to apparatus for testing vehicle and combustion emissions.

BACKGROUND OF THE INVENTION

Current federal and most state regulations require automobile emission tests according to a defined procedure on a regular basis. These tests are conducted either at a government operated test facility or at designated private facilities. In addition, the increased interest in emissions as they effect air quality has resulted in substantial laboratory and field research into combustion by-products, particularly those from fossil fuel combustion.

Combustion emissions, especially those from motor vehicles, are normally tested for total unburned hydrocarbons, carbon monoxide, carbon dioxide, and oxides of nitrogen. Testing methodology includes non dispersive infrared (NDIR) for carbon monoxide and carbon dioxide, chemiluminescence (CLD) for oxides of nitrogen and flame ionization detection (FID) for unburned hydrocarbons.

In many areas of the United States vehicle emission testing equipment can comprise the so-called "repair grade" analyzers which, although of relatively modest price, are also of moderate accuracy and are used primarily for raw exhaust measurements. Repair grade analyzers are not suitable for more accurate emission testing. The Environmental Protection Agency has published guideline procedures, emission standards and equipment specifications for inspection and maintenance (I/M-240) equipment as set forth in EPA-AA-EPSD-IM-93-1 specifications dated April 1994 relating to high tech I/M procedures, emission standards, quality control requirements and equipment specifications. These specifications require instruments having much higher sensitivities (0–50 ppm) and have complex linearity, temperature and long term stability and interference specifications. Such instruments are referred to herein as "research grade" instruments. Higher sensitivity analyzers and procedures requiring the use of such analyzers are currently required in areas of the United States, deemed non attainment, i.e. with excess air pollution levels. This equipment is expensive, difficult to maintain and requires a relatively large installation and operation area and a high volume of tests to justify the expense. Small laboratories and small emission test facilities find it very difficult to justify purchasing such equipment and many do not have the space necessary or the test volume to operate such equipment.

Accordingly it would be desirable to have compact, portable emission testing equipment suitable for use in small testing facilities and laboratories that is relatively inexpensive and that produces results comparable to the I/M-240 equipment.

SUMMARY OF THE INVENTION

The present invention provides an emission testing system which produces research grade results while at the same time is compact and inexpensive to manufacture, procure and maintain. The system includes at least one non-dispersive infrared (NDIR) unit, a chemiluminescence detector (CLD) unit and a flame ionization detection (FID) unit. All of the analytical units are incorporated in the system for operation with a sample which has been subjected to a single conditioning step. In this manner each analytical unit tests a uniformly conditioned sample. The system is capable of sampling both raw emissions for raw emission idle tests (BAR 90) and dilute volume samples for dilute volume sample mass emission tests under IM-240 regulations. An interface/computer module interfaces with the system for data readout and report production as well as carrying out system maintenance programs.

More particularly, the system includes a single housing in which are disposed a sampling module, a conditioning module, an analyzer module and an interface/computer module. The sampling module includes a raw exhaust probe and a dilute volume sampler. The dilute volume sampler accurately measures flow which is incorporated into all calculations. The need for separate flow control means in the system is eliminated. The conditioning module filters and removes moisture from the sample as it enters the system and provides a uniformly conditioned sample for the analyzer module. The analyzer module contains research grade NDIR analyzers for carbon monoxide, carbon dioxide and for hydrocarbons in raw emission samples. The analyzer module further includes an FID unit for the measurement of total hydrocarbons in the dilute volume sample stream and a CLD unit for oxides of nitrogen. The interface/computer module includes the necessary software for calibration and analysis procedures. The entire system is contained in a roll around cabinet.

Although not essential, this system may include a zero gas generator for producing instrument air for the CLD and FID units. This eliminates the need for a separate source of clean instrument air. The system may also include a hydrocarbon verification system to check the accuracy of the dilute volume sampler.

Other advantages and features of the system of the present invention will become apparent from the following detailed description taken in conjunction with the drawings.

DESCRIPTION OF THE PREFERRED EMBODIMENTS

Figure 1:
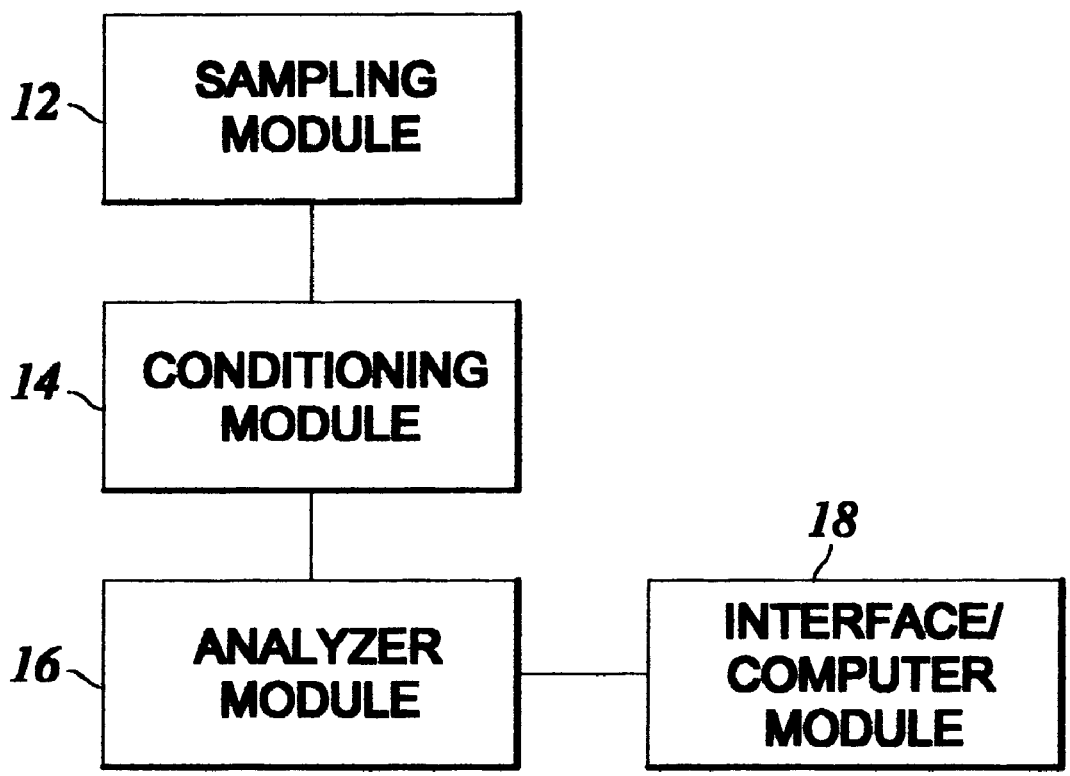
FIG. 1 is a block diagram of the system of the present invention.
Figure 2:
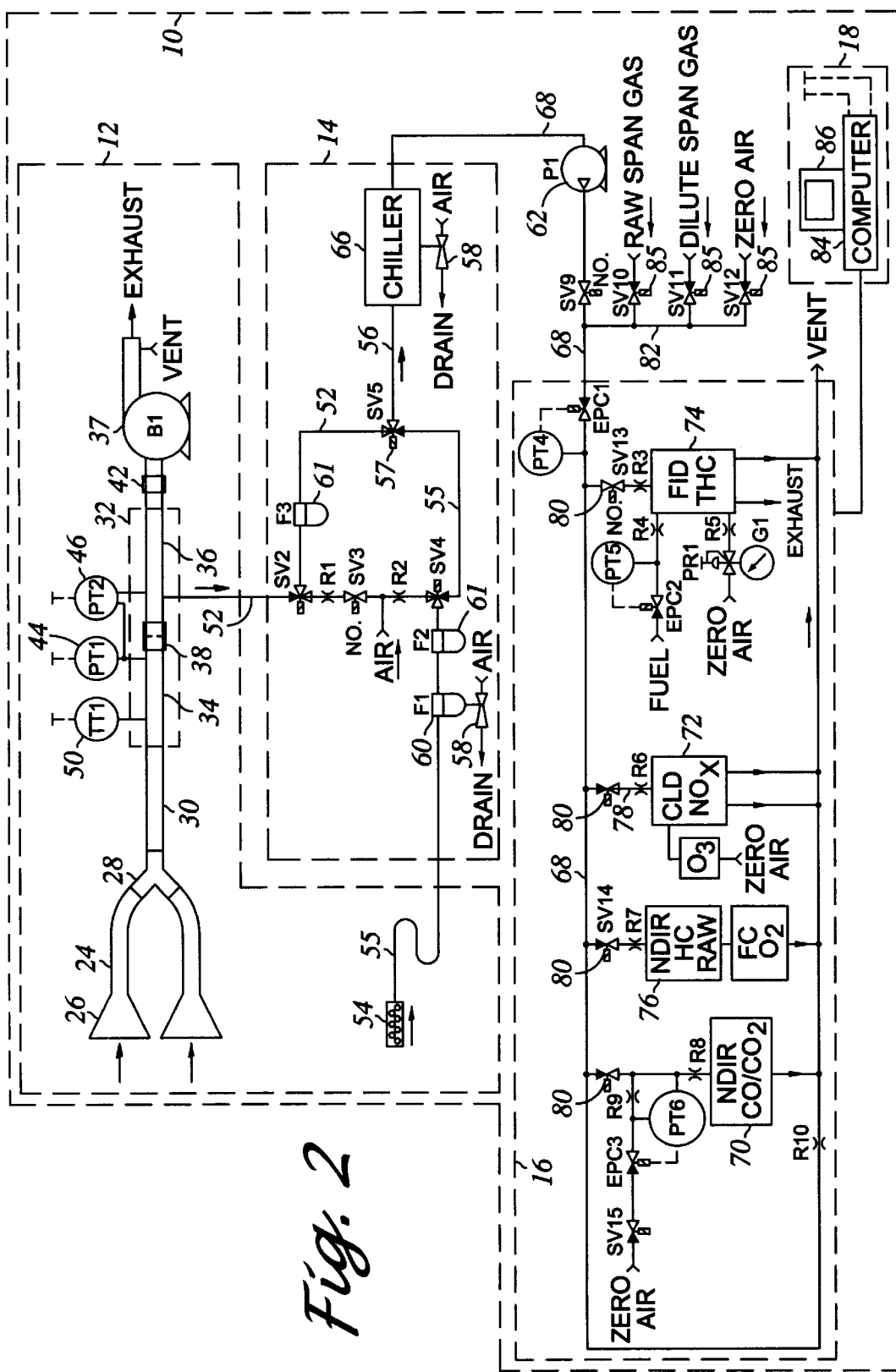
FIG. 2 is schematic flow diagram of one embodiment of the system of the present invention.

Referring to FIGS. 1 and 2, the system of the present invention, illustrated generally as 10, is most conveniently described as comprising a series of modules. The system comprises a sampling module 12, a conditioning module 14, an analyzer module 16 and an interface/computer module 18.

The sampling module 12 includes a probe 54 for sampling raw emissions and a dilute volume sampling unit 32 for controlled dilute volume sampling. The raw sample or the dilute volume sample is passed through the conditioning module 14 for removal of excess particulates, excess moisture and for flow control. After conditioning, the sample is led to the analyzer module 16 for flow control and analysis of the emission by-products such as total hydrocarbons, oxides of nitrogen, carbon monoxide and carbon dioxide. The analyzer module 16 contains the necessary research grade analytical units for conducting the various analyses. The output signals of the analytical units are received by the interface/computer module which converts the signals into meaningful emission concentrations which can be read out on a monitor or printed on a conventional printer.

It will be understood that the system of the present invention can be used for the measurement of emission by-products from various sources such as, for example, smoke stack emissions, ambient air sampling, vehicle exhaust emissions and the like. However, for the purposes of describing the system herein, the system will be illustrated and described in connection with the testing of vehicle emissions. In that connection it will be understood that the emission collector of the sampling module 12 is designed for the collection of vehicle exhaust but it may be modified for emission collection to accommodate the particular type of emission source being tested.

As best shown in FIG. 2, the sampling module 12 consist of a collecting tube 24 having a collection funnel 26 at one end. Since many vehicles have twin exhaust pipes, a pair of the collecting tubes 24 are used and the collection funnel 26 of each is placed in close proximity to the exhaust pipes of the vehicle for collection of the exhaust and also background air immediately surrounding the exhaust pipe. The collecting tubes 24 communicate with a stainless steel "Y" unit 28 where the respective streams from each of the collecting tubes are combined in the main sampling tube 30. In the embodiment shown both the collecting tubes 24 and the main sampling tube 30 are four inch silicon tubes. If the vehicle has a single exhaust pipe, one side of the "Y" unit 28 is sealed with a cap (not shown).

Figure 3:
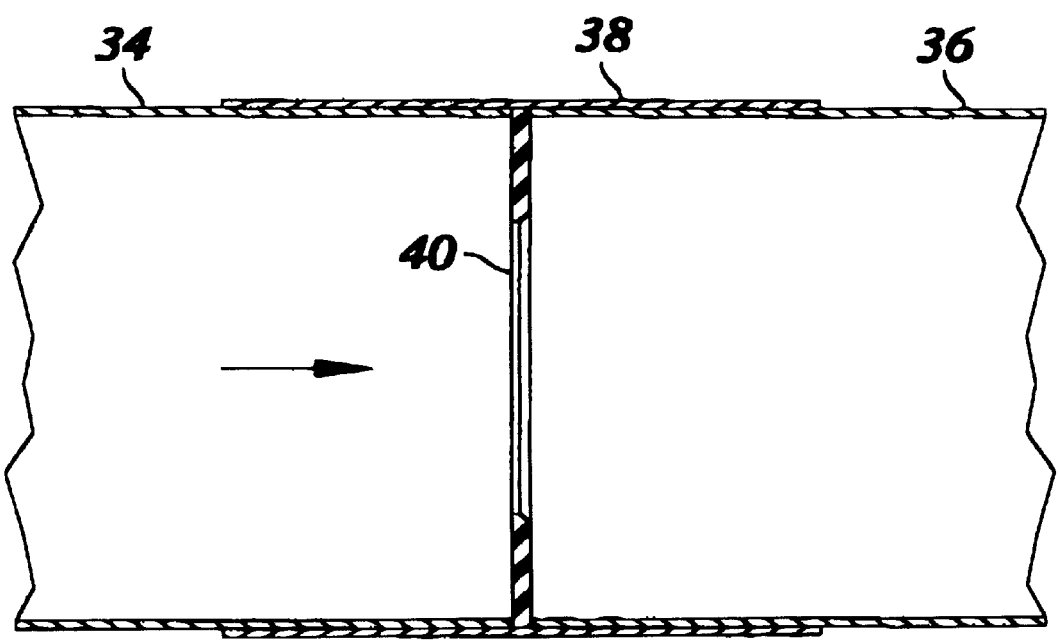
FIG. 3 is a schematic diagram of the orifice section of the sampling module of FIG. 2.

The main sampling tube 30 communicates with the dilute volume sampling unit 32 which consists of a first section of stainless steel tubing 34 and a second section of stainless steel tubing 36 which are connected by an orifice assembly coupler 38 (FIG. 3). The orifice assembly coupler 38 consists of a short length of stainless pipe having a bore of approximately the same size as, or very slightly larger than, the outside diameter of the first and second sections, 34 and 38, of stainless tubing. The end portions of the first and second sections, 34 and 36, are received in the stainless pipe for coupling the tube sections. A square edge orifice 40 (FIG. 3) is disposed in the coupler 38 for restricting the flow of the combined exhaust and background air streams between the first section 34 and the second section 36 of the stainless tubes. A silicon sleeve 42 communicates between the second stainless steel tube section 36 and a blower 37 which serves to draw the main combined background air and exhaust sample through the sampling module 12. An upstream precision pressure transducer 44 in the first stainless steel tube section 34 on the upstream side of the square edge orifice 40 is provided for measuring the inlet pressure of the square edge orifice. A precision differential pressure transducer 46 connected in the second stainless steel tube section 36 downstream of the square edge orifice 40 is provided to measure the differential pressure across the square edge orifice. The pressure transducers, 44 and 46, are electrically connected to the I/O module 18. A thermocouple 50 is also located in the first stainless steel pipe section 34 for measuring the temperature of the stream on the upstream side of the square edge orifice 40. The thermocouple 50 is also electrically connected to the I/O module 18. When the system 10 is in operation, software at the I/O module 18 continuously calculates the mass flow rate of the combined exhaust and background air stream based on differential pressure and temperature and provides an output signal of mass flow which is incorporated in the calculation of emission concentrations. While the foregoing describes a preferred system for the determination of flow rate it will be understood that other devices for creating and measuring a differential pressure in a tube are known in the art and can be used in the present invention to determine the mass flow of the combined background air and emission exhaust streams in the main sampling tube 30.

A portion of the combined background air and emission stream is withdrawn from the tube section 36 through a dilute sample line 52. The withdrawn sample is conditioned for subsequent analysis according to IM-240 procedures as will be described below.

For raw emission analysis, such as under the BAR 90 procedures, the sample probe 54 collects the raw exhaust emissions directly from the exhaust pipe of the vehicle and, by means of the raw emission line 55, the sample is led to the conditioning module 14 where the raw exhaust sample is passed directly to a coalescing filter 60 and then to a particulate filter 61. The condensate from the sample is removed from the coalescing filter 60 by an aspirator 58.

It is preferred to combine the collector tubes 24 and the raw emission probes 54 in a single assembly. Although shown separately in FIG. 2, it will be seen that a raw emission probe 54 can be located in each of the collector tubes and that the raw emission line 55 can be disposed in the main sampling tube 30 for conducting the raw emission sample to the filters 60 and 61 and the aspirator 58. In this embodiment, the raw emission probe 54 is a stainless steel tube ¼ inch in diameter and the raw emission line 55 is ¼ inch Teflon tube. It will be seen that the much smaller raw emissions probe 54 and tube will not interfere with the flow of combined exhaust emission and ambient air through the collecting tubes 24 and the main sampling tube 30 when operating the system under IM-240 procedures.

The dilute sample line 52 and the raw emission line 55 both communicate with a chiller 66 through a line 56 in which is disposed a valve 57 for closing either the dilute sample line 52 or the raw emission line 55 depending on the analytical procedure being conducted. Additional valving (not shown) can be provided to back flush the lines with air when not in use. The sample is passed through the chiller 66 to remove condensed water and water vapor prior to analysis. Good results have been obtained using a waterless chiller unit identified as the Model 1100 OEM Waterless Chiller manufactured by California Analytical Instruments, Inc., Orange Calif. The waterless chiller unit 66 operates by circulating the sample gas through approximately ten feet of ¼ inch tubing which is contained in larger bore tubing through which is circulated a coolant maintained at a temperature of between 3° C. and a 10° C. Moisture condensed from the cooled sample is removed by means of an aspirator 58 and passes to a drain (not shown).

All samples, regardless of whether they comprise diluted samples for analysis under IM-240 or comprise raw emissions to be analyzed under BAR 90 procedures, are subjected to the same conditioning. Differences in sample condition between the various analyzers are eliminated and all analyses are made on samples which have been subjected to the same conditioning steps so that sample integrity is maintained throughout the system.

A conditioned sample line 68 in which is disposed a pump 62 conducts the conditioned sample to the analyzer module 16. As illustrated, the analyzer module 16 contains five research grade gas analyzer units although it will be understood that the analyzer module 16 may contain fewer or additional units as required. The analyzers are the same "Research Grade" analyzers used in federal test procedures and in many states in the IM-240 systems.

For IM-240 analysis procedures, the module 16 contains an NDIR unit 70 for carbon monoxide analysis and for carbon dioxide analysis. In addition a CLD unit 72 is provided for NOx analysis. A FID unit 74 is provided for the analysis of the total hydrocarbons pursuant to IM-240 test procedures. An NDIR unit 76 is also provided for the analysis of hydrocarbons in the raw emission samples under BAR 90 procedure. Each unit communicates with the sample line 68 by a line 78 which is provided with valves 80 for shutting off sample flow to the analyzer units as desired.

The hydrocarbons analyzer 74 utilizes the flame ionization principle for the measurement of total hydrocarbons in the diluted sample stream. The analyzer 74 uses hydrogen and helium fuel for the burner which is supplied by a high pressure cylinder (not shown) contained in the system 10.

The CLD 72 employs the light output from the chemiluminescence reaction between ozone and NO formed by converting NOx to NO. The light is sensed by a photo diode detector. This principle is employed in equipment currently used in vehicle certification laboratories. This analyzer is designed to provide the necessary safety protection required by OSHA to adequately monitor the 8 hour time weighted average background air concentration which should be less than 25 ppm NO.

A calibration gas line 82 communicates with the conditioned sample line 68. The calibration gas line 82 further communicates with a source of raw and dilute calibration gas and a source of zero air gas for calibrating the gas analyzer units of the analyzer module 16. Valves 85 inserted in the lines between the calibration gas line 82 and the source of calibration gas control the gas flow to the analyzer units.

The interface/computer (I/O) module 18 includes a computer 84 and monitor 86. The computer 84 receives the output signals from the analyzer units as well as the flow rate signal from the sampling module 12. The computer 84 is programmed to compute concentrations of the emission products including in the computations the mass flow rate of the dilute sample gas through the sampling unit 32. The computer 84 is also programmed with both the test procedures for dilute volume sample mass emission tests under the IM-240 test procedures and for the BAR 90 raw emission tests. In addition input/output parameters and test reports are available from the computer 84 for system maintenance.

The operation of the system 10 is illustrated in connection with the analysis of a dilute volume sample where the collecting funnel 26 is located adjacent to the outlet of the exhaust pipe of a vehicle for collecting the emissions and ambient air immediately surrounding the exhaust pipe. The emissions samples, thus diluted, are drawn through the collecting tube 24 by the blower 37. The sample passes through the main sampling tube 30 to the sampling unit 32 and through the square edge orifice 40. The pressure differential produced by the orifice is measured by the upstream and downstream precision differential pressure transducers 44 and 46 and the output therefrom is communicated to the I/O module 18. The temperature of the diluted sample stream is measured by the thermocouple 50 and the output thereof is also communicated to the I/O module 18. A proportion of the dilute sample is extracted from the main sampling tube 36 and is conducted through the dilute sample line 52 through the particulate filter 61 to the chiller 66 for removal of water vapor and water from the sample. Condensed water is removed through the aspirator 58 to a drain. The conditioned sample is conducted through the sample line 68 to the analyzer module 16. Pursuant to IM-240 test procedures the sample is analyzed for total hydrocarbons at the FID analyzer 74 and for oxides of nitrogen at the CLD unit 72. A portion of the sample is also analyzed for carbon dioxide and for carbon monoxide by the NDIR unit 70. The output signal from the analyzers is directed to the I/O module 18 which is programmed to calculate the concentration of the sought for components incorporating into the calculations the temperature and mass flow of the dilute sample through the sampling module 12.

The analysis of raw emissions pursuant to BAR 90 test procedures is carried out in a procedure similar to the dilute sample procedure described above. The probe 54 is inserted in the exhaust pipe of a vehicle and the raw emissions are passed through the coalescing filter 60 and the particulate filter 61 to remove gross particulates and moisture and then to the chiller 66 for conditioning as described above. The raw emissions are drawn by an sampling pump 62 through the raw emission line 55. From the chiller 66, the conditioned raw emission sample passes through the sample line 68 to the analyzer module 16. In the case of raw emissions, the valve 80 leading to the FID unit 74 is closed and the valve 80 and to the NDIR unit 76 is opened for the determination of unburned hydrocarbons. Portions of the sample are also tested for carbon dioxide and for carbon monoxide at the NDIR unit 70 and for oxides of nitrogen at the CLD unit 72.

From time to time the system analyzers are calibrated with calibration gas containing known amounts of the sought for emission products. Valves 85 inserted in the lines between the calibration gas line 82 and the source of the calibration gases are positioned to permit the flow of calibration gas to the analyzer module 16 for instrument calibration in a conventional manner consistent with the analyzer being calibrated.

The components of the system, as described above, can be compactly contained in a roll around cabinet which makes the system portable and flexible for use in small shops and in laboratories. As mentioned above, the components of the analyzer module 16 are research grade analyzers and the results obtained using the system 10 of the present invention are comparable to the large expensive fixed units employed in large emission testing centers and in many laboratories conducting research on combustion products. The flexibility and portability of the system 10 of the present invention allows the system to be used for many applications involving the testing of combustion emission products and, as mentioned above, the system is not limited to the testing of vehicle emissions.

As will be understood, certain of the analyzer units, such as the CLD unit 72 and the FID unit 74 require a source of clean instrument air in order to operate properly. Pursuant to proposed quality standards, instrument air must contain less than 0.3 ppm of oxides of nitrogen, less than 0.1 ppm total hydrocarbons, less than 0.5 ppm carbon monoxide and less than 1 ppm carbon dioxide in order to meet EPA and California quality specifications for instrument air. Conventional compressed air, normally available in most shops and laboratories, cannot be used as a direct source of instrument air for the system 10 of the present invention. With the larger fixed installations, instrument air is produced by zero air generators that are designed for very high flow rates, greater than 40 liters/minute, and are typically only used in facilities with multiple test lanes which can support the zero air generator cost. For smaller installations, clean instrument air is supplied as compressed air in high pressure cylinders. In accordance with the present invention, an embodiment of the system 10 includes a zero grade air module which is compact and which can be incorporated in the roll around cabinet for the production of instrument air which meets California and the EPA standards.

Figure 4:
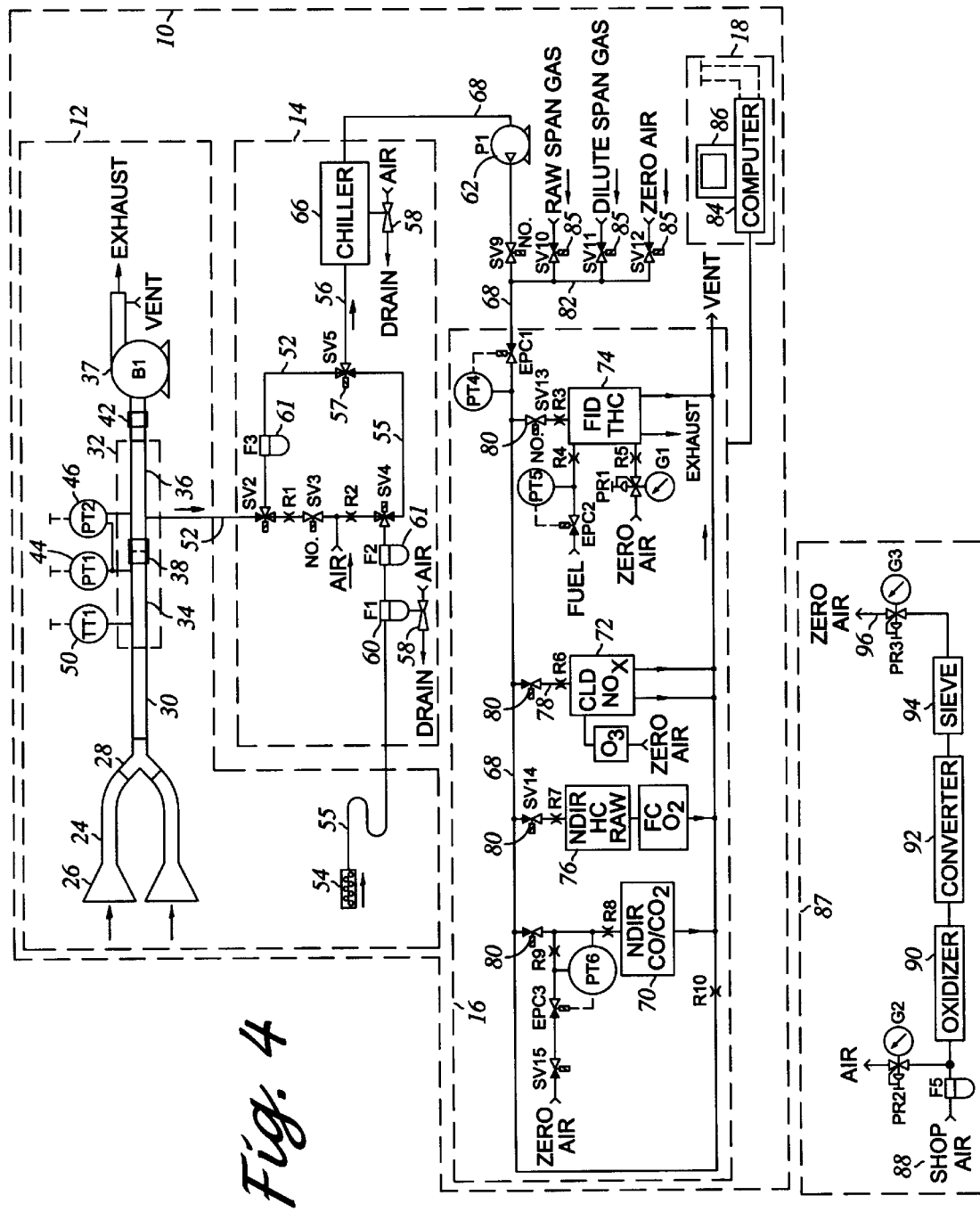
FIG. 4 is a schematic flow diagram of yet another embodiment of the system of the present invention including apparatus for producing zero grade instrument air.

Referring to FIG. 4, where like reference numbers denote like parts, the system 10 includes a zero air module 87 consisting of a source of compressed air 88, which may be ordinary shop compressed air. The compressed air 88 is passed through a catalytic oxidizer 90 for oxidation of hydrocarbons in the compressed air, such as for example oil, to carbon dioxide and carbon monoxide. The air is then passed through an ultraviolet radiation converter 92 for the conversion of oxides of nitrogen to $NO_2$. The treated air is then passed through at least one molecular sieve 94 for removal of a major portion of the carbon monoxide, carbon dioxide and $NO_2$. The clean instrument air thus produced is conducted through a line 96 to the chemiluminescence reactor unit 72 for production of ozone necessary for the chemiluminescent reaction and to the flame ionization detector 74 for incorporation in the air/fuel mixture. The zero air generator system of the type used in the system 10 is more fully described in copending application Ser. No. 08/700, 337 filed Aug. 8, 1996. Instrument air produced by the zero air module 87 has been tested and found to meet or exceed the standards set for instrument air by the EPA and California regulations.

Figure 5:
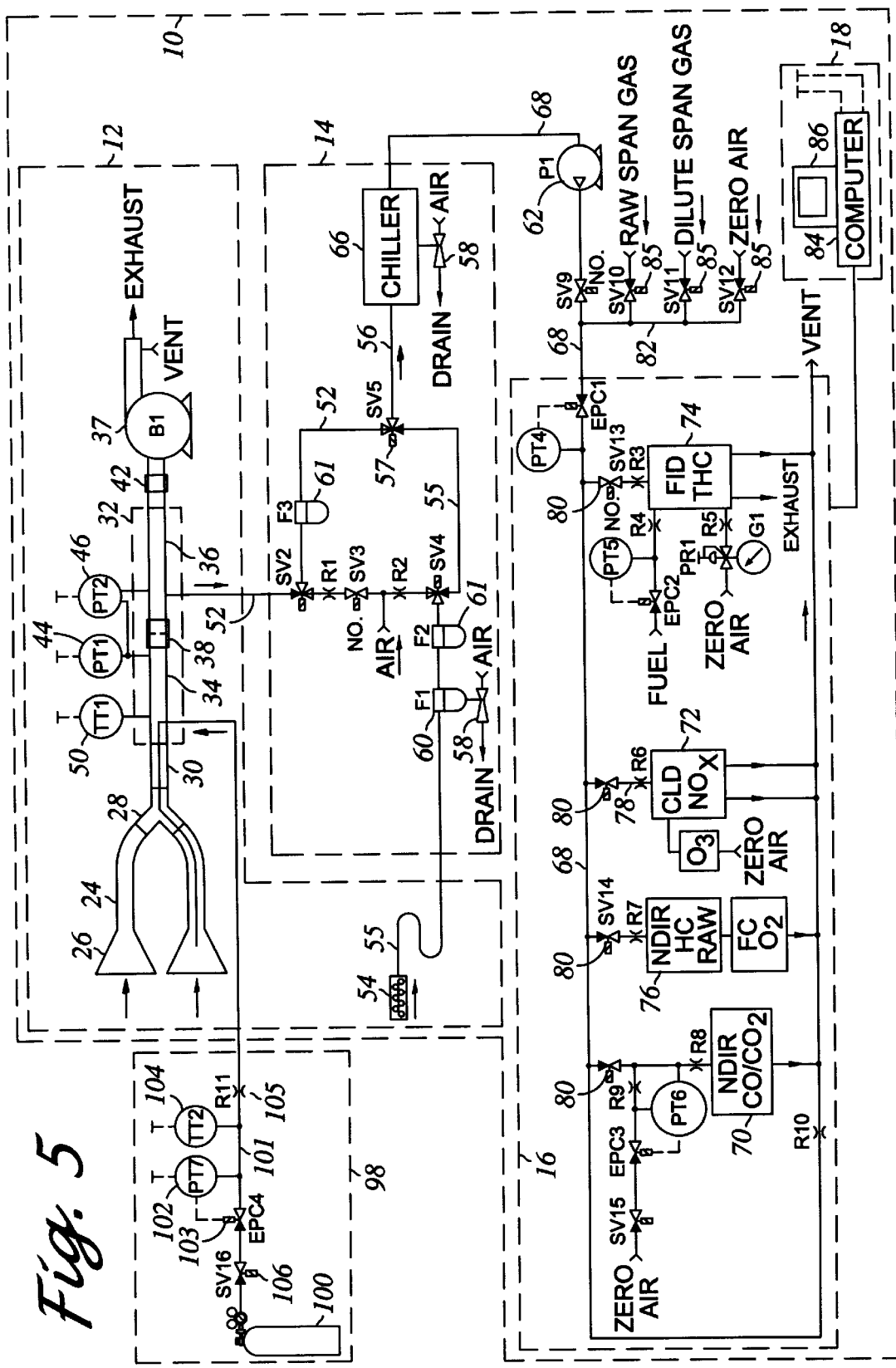
FIG. 5 is a schematic flow diagram of another embodiment of the system illustrating the inclusion of a hydrocarbon calibration check for the dilute volume sampler.

In another embodiment of the invention, as illustrated in FIG. 5, the system 10 includes a flow verification module 98 consisting of a hydrocarbon injection system for testing the accuracy of the volume sampler portion of the sampling module 12. Referring to FIG. 5, the hydrocarbon (propane or butane) injection system includes a source of hydrocarbon 100, a line 101 for introduction of the test gas into the collecting tube 24, a high pressure transducer 103 coupled to a regulator 103, a shut off valve 106, a precision temperature probe 104, and precision restricter 105. The verification module 98 should be compact for incorporation in the roll around cabinet which contains the system 10. Good results have been obtained utilizing the hydrocarbon injection system manufactured by California Analytical Instruments, Inc., Orange, Calif. It will be understood, however, that verification of dilute volume sampling systems utilizing propane is known in the art and does not per se form a part of the present invention except as combined in the system 10.

In operation, a known amount of hydrocarbon at a known temperature is introduced for predetermined amount of time in to the collecting tube 24. The temperature and pressure measurements from the verification system are directed to the I/O module 18.

The readings from the verification system and from the sampling module 12 are compared to insure that the data from the sampling module is accurate and that the correct mass of emission gases are being sampled and reported by the system 10. An error of more than 4% exceeds IM-240 specifications and corrective action is required.

The present invention provides a compact portable emission testing system capable of providing results comparable to those of laboratory apparatus or, in the case of vehicle emission testing, large multi lane fixed units. The system meets the test specifications of IM 240 and BAR 90 for raw emissions promulgated by the E.P.A. The system of the present invention is compact and highly portable and thus is adaptable for use in small emission testing laboratories and vehicle emission testing shops. In addition to being compact and portable, the unit is manufactured at less cost than for the large emission testing systems. In its preferred embodiment, the system of the present invention includes all of necessary test procedures and apparatus for calibrating the analytical units and for providing internal testing of the system as required by EPA regulations.

As will be understood, various arrangements which lie within the spirit and scope of the invention other than those described in detail in the specification will occur to those persons skilled in the art. It is therefore to be understood that the invention is to be limited only by the claims appended hereto.

Having described the invention, we claim:

1. A system for mass emission sampling of combustion products comprising:
   a. a sampling module including a dilute volume sampler and a raw emission sampler;
   b. means for drawing a proportional sample from said dilute volume sampler; said means including a square edge orifice for restricting the flow of the combined exhaust and background air streams;
   c. a single conditioning module for conditioning both said sample from said dilute volume sampler and said raw emission sampler prior to analysis;
   d. an analyzer module for analyzing a conditioned sample for emissions, said analyzer module comprising at least two different analyzers; and
   e. an interface/computer module for analyzing the data from said analytical module and for controlling said system.

2. The system of claim 1 wherein said modules are contained in a single housing.

3. The system of claim 1 further including a zero gas generating module for generating instrument air for said analyzer module.

4. The system of claim 1 further including a hydrocarbon injection system for monitoring the accuracy of the dilute volume sampler.

5. The system of claim 1 wherein said dilute volume sampler of said sampling module consists of a collection tube having a collection funnel at one end thereof, a main sampling tube communicating with said collection tube and a mass flow sampling unit comprising tubing in which is disposed a square edge orifice for restricting the flow through said flow sampling unit a pressure port communicating with said sampling unit on the upstream aside of said orifice and a second pressure port communicating with said sampling unit at the downstream side of said orifice for sensing pressure at each side of said orifice, means conducting said pressure sensings to said interface/computer module and temperature sensing means communicating with said interface/computer module for sensing the temperature of said sample flowing through said sampling unit and for transmitting said temperature to said interface/computer module.

6. The system of claim 1 wherein said raw emission sampler of said sampling module comprises a sample probe for collection of raw emissions, a raw sample line for conducting said raw emission sample to said conditioning unit, and an aspirator and filter in said raw sample line for removing gross particles and condensed moisture from said raw emission sample.

7. The system of claim 5 wherein the inside diameter of said collecting tube and said main sample tube of said controlled volume sampler is larger than the outside diameter of said sample probe and said raw emission line and said raw emission probe are contained within said dilute volume sampler.

8. The system of claim 1 wherein said conditioning module includes a line for conducting all sample flow from said sampling unit to said conditioning module, a precision flow controller for creating a predetermined flow rate through said system and chiller for removing moisture from said sample whereby all sample is subjected to the same conditioning regardless of whether it is a raw emission sample or a dilute sample from said dilute volume sampler.

9. The system of claim 1 wherein said analyzer module comprises at least analyzer for the analysis of at least one of an emission component selected from the group consisting of carbon monoxide, carbon dioxide, oxides of nitrogen, total hydrocarbons and total unburned hydrocarbons.

10. The system of claim 1 wherein said analyzer module comprises a chemiluminescence detector analyzer for the determination of oxides of nitrogen, a flame ionization detector analyzer for the determination of total hydrocarbons, a non-dispersive infrared analyzer for the determination of carbon monoxide and carbon dioxide.

11. The system of claim 10 wherein said analyzer module further includes a non-dispersive infrared analyzer for the determination of hydrocarbons in said sample from said raw emission samplers.

12. The system of claim 10 wherein each said analyzer communicates through a common line with said conditioning module.

13. The system of claim 1 further including a hydrocarbon verification monitoring unit for testing the accuracy of said dilute volume sampler.

* * * * *